United States Patent
De Villiers

(10) Patent No.: US 8,281,745 B2
(45) Date of Patent: Oct. 9, 2012

(54) SYSTEM AND METHOD FOR MANAGING ANIMALS ON A DAIRY FARM

(75) Inventor: Pierre De Villiers, Pretoria (ZA)

(73) Assignee: DeLaval Holding AB, Tumba (SE)

( * ) Notice: Subject to any disclaimer, the term of this patent is extended or adjusted under 35 U.S.C. 154(b) by 440 days.

(21) Appl. No.: 12/307,758

(22) PCT Filed: Jul. 7, 2006

(86) PCT No.: PCT/SE2006/000852
§ 371 (c)(1),
(2), (4) Date: May 20, 2009

(87) PCT Pub. No.: WO2008/004918
PCT Pub. Date: Jan. 10, 2008

(65) Prior Publication Data
US 2009/0288605 A1    Nov. 26, 2009

(51) Int. Cl.
*A01J 5/007* (2006.01)

(52) U.S. Cl. ............... 119/14.08; 119/14.14; 119/14.17; 119/53

(58) Field of Classification Search ............... 119/14.02, 119/14.08, 14.14, 14.17, 14.18, 51.02, 52.4, 119/53; *A01J 5/00, 5/007; A01K 5/00, 5/02*
See application file for complete search history.

(56) References Cited

U.S. PATENT DOCUMENTS

| | | | | |
|---|---|---|---|---|
| 5,152,246 A | * | 10/1992 | Wakui et al. | 119/14.15 |
| 5,988,106 A | * | 11/1999 | van den Berg | 119/51.02 |
| 6,619,228 B2 | | 9/2003 | Voogd et al. | |
| 6,776,119 B2 | | 8/2004 | Vijverberg et al. | |
| 6,863,023 B2 | * | 3/2005 | Burghardi et al. | 119/51.02 |
| 6,981,466 B2 | * | 1/2006 | Lindholm | 119/14.02 |
| 7,236,237 B2 | * | 6/2007 | Schmilovitch et al. | 356/73 |
| 2002/0000204 A1 | * | 1/2002 | van der Lely et al. | 119/14.02 |
| 2002/0124803 A1 | | 9/2002 | Chen et al. | |

(Continued)

FOREIGN PATENT DOCUMENTS

EP      0 896 222      2/1999
(Continued)

OTHER PUBLICATIONS

International Search Report dated Feb. 12, 2007, from corresponding PCT application.

(Continued)

*Primary Examiner* — Rob Swiatek
*Assistant Examiner* — Kathleen Iwasaki
(74) *Attorney, Agent, or Firm* — Young & Thompson

(57) ABSTRACT

A management system for managing animals on a dairy farm includes a receiving element (12) provided for receiving, for each of the animals, a value of a protein content and a value of a fat content of milk from the animal as milked on the dairy farm; a calculating element (19) provided for calculating, for each of the animals, the ratio of the values of the protein and fat contents of milk from the animal; a comparison element (20) provided for fetching, for each of the animals, from a database (18) a reference protein/fat ratio, and for comparing the calculated protein/fat ratio with the reference protein/fat ratio; and a notifying element (21-23), preferably a display unit (21) or a loudspeaker (22), provided for notifying, for each of the animals, a dairy farmer (24) of the dairy farm depending on the outcome of the comparison.

26 Claims, 2 Drawing Sheets

U.S. PATENT DOCUMENTS

| | | | |
|---|---|---|---|
| 2003/0061994 A1 | 4/2003 | Vijverberg et al. | |
| 2003/0226508 A1* | 12/2003 | Theelen | 119/14.02 |
| 2004/0154548 A1* | 8/2004 | Eriksson | 119/14.08 |
| 2006/0054092 A1* | 3/2006 | Valencia et al. | 119/51.02 |
| 2006/0249082 A1* | 11/2006 | Holmertz et al. | 119/14.02 |

FOREIGN PATENT DOCUMENTS

| | | |
|---|---|---|
| EP | 1 212 938 | 6/2002 |
| EP | 1 297 743 | 4/2003 |
| EP | 1 297 744 | 4/2003 |
| EP | 1 300 074 | 4/2003 |
| GB | 2 283 091 | 4/1995 |
| WO | WO 2005067704 A1 * | 7/2005 |

OTHER PUBLICATIONS

A. Brand et al., "Herd Health and Production Management in Dairy Practice", handbook chapter 4, part 2, pp. 223-281, 2001, Wageningen Pers, The Netherlands.

* cited by examiner

SYSTEM AND METHOD FOR MANAGING ANIMALS ON A DAIRY FARM

TECHNICAL FIELD OF THE INVENTION

The present invention generally relates to dairy farming, and more specifically the invention relates to a system and to a method, respectively, for managing animals on a dairy farm.

DESCRIPTION OF RELATED ART AND BACKGROUND OF THE INVENTION

Feed costs comprise 40-50% of the cost of milk production. Implementation and management of feeding systems to sustain high levels of milk production and control feed costs are crucial to the profitability of expanding dairies. Considerations regarding nutritional demands of the herd (including grouping), ration management (includes analysis of the feed, cost and availability), feed preparation and transport, feed distribution and consumption control have to be made.

Attempts have been made to increase the efficiency of feed utilization and milk production by using various formulations and feed supplements. Despite continued improvement in the development of dairy cattle feed rations, it is desirable to further increase the efficiency of feed utilization and milk production by dairy cattle.

SUMMARY OF THE INVENTION

It is an object of the present invention to provide a system and to a method, respectively, for managing animals on a dairy farm, which can reduce the feeding costs and increase the quantity and/or quality in milk production simultaneously as the animal health is improved.

It is a further object of the invention to provide such a system and such a method, which can reduce problems related to feeding and metabolic diseases such as ketosis and displaced abomasum.

It is yet a further object of the invention to provide such a system and such a method, which can be fully automated, and which can be coupled to a computer-based managing and control device for overall management of the animals on the farm.

It is still a further object to provide such a system and such a method, which are efficient, accurate, precise, flexible, fast, uncomplicated, reliable, of reasonable cost, and/or easy to implement and use.

These objects, among others, are according to the present invention attained by systems and methods as specified in the appended claims.

According to one aspect of the invention there is provided a system for managing animals on a dairy farm comprising a dairy herd system, which includes a receiver, calculating and comparing modules and a notifying apparatus. The receiver receives, for each of the animals, values of protein and fat, preferably butterfat, contents of milk from the animal as milked on the dairy farm. The calculating and comparing modules (i) calculate, for each of the animals, the ratio of the values of the protein and fat contents of milk from the animal, (ii) fetch, for each of the animals, a reference protein/fat ratio from a database of the dairy herd system, and (iii) compare the calculated protein/fat ratio with the fetched reference protein/fat ratio. Finally, the notifying apparatus is controlled to notify, for each of the animals, a dairy farmer of the dairy farm depending on the outcome of the comparison of the calculated protein/fat ratio and the fetched reference protein/fat ratio. Preferably, a notification is made for an animal if the calculated protein/fat ratio differs from the reference protein/fat ratio by at least a given amount. Such discrepancy indicates a metabolic disorder.

By such a system the farmer can be alerted when an animal produces milk with an abnormal protein/fat ratio so that he/she can investigate the reasons behind the discrepancy and take necessary actions. The reasons are most typically that the feeding of the animal is not optimized. Thus, the invention enables the farmer to track the effect of forage and concentrate metabolism in the heard.

If the protein/fat ratio is higher than normal it is an indication of an unbalanced feed, such as a feed having an unbalanced fiber content, supplied to the animal, and if the protein/fat ratio is lower than normal it is an indication of an unbalanced feed, such as a feed having unbalanced type of protein and/or energy content, supplied to the animal. Proper correction of the feed rationing may be performed based on the notification. However, care has to be taken to the breed, the lactation phase and age or number of lactations of each animal since the protein/fat ratio is highly dependent on those factors.

If the protein/fat ratio differs very much from normal, a veterinarian may be automatically notified, e.g. via wireless or wired telephony, or via the Internet.

The protein and fat contents may be automatically measured on the farm by stand-alone analyzer devices such as a NIR instrument and optionally a fat droplet counter. The absolute values of the protein and fat contents may be notified to the farmer since they may provide additional information.

The reference protein/fat ratio may be obtained, for each animal, from a large regional or national dairy animal database, or it may be calculated in the dairy herd system based on historical protein/fat ratio data from milk from the animal, and optionally on historical protein/fat ratio data from milk from other animals, preferably from animals having similar breed, lactation phase, and age and as the animal.

In order to facilitate the handling and to provide statistical basis, the animals may be divided into groups depending on certain parameters such as e.g. number of days in lactation. A common reference protein/fat ratio may be determined for all the animals within a given group.

The dairy herd system may be connected to at least one of a feed mixer apparatus, a feeding apparatus, an animal-operating apparatus, and a milking equipment-operating apparatus and adapted to control the device(s) in response to the comparison of the of the calculated protein/fat ratio and the fetched reference protein/fat ratio for a give animal.

Thus, under the control of the dairy herd system the feed mixer apparatus may be provided for automatically alter the mixing of feed for an animal if the calculated protein/fat ratio for that animal differs from the reference protein/fat ratio for that animal by at least a given amount.

Alternatively or additionally, the feeding apparatus may be provided for automatically alter the feeding of an animal, the animal-operating apparatus may be provided for automatically treating the animal, and/or the milking equipment-operating apparatus may be provided for automatically performing a milking equipment-related operation in connection with the milking of the animal if the calculated protein/fat ratio for the animal differs from the reference protein/fat ratio for the animal by at least a given amount.

According to another aspect of the invention there is provided a method for managing animals on a dairy farm comprising the steps of: receiving, for each of the animals, a value of a protein content and a value of a fat content of milk from the animal as milked on the dairy farm, calculating, for each of the animals, the ratio of the values of the protein and fat contents of milk from the animal, fetching, for each of the animals, a reference protein/fat ratio from a database, comparing, for each of the animals, the calculated protein/fat ratio with the fetched reference protein/fat ratio, and notifying, for each of the animals, a dairy farmer of the dairy farm depending on the outcome of the comparison of the calculated protein/fat ratio and the fetched reference protein/fat ratio.

The method is preferably performed on a regular basis, e.g. each time an animal is milked or once a day for each animal.

Further characteristics of the invention and advantages thereof, will be evident from the following detailed description of preferred embodiments of the present invention given hereinafter and the accompanying FIGS. 1-2, which are given by way of illustration only and thus, are not limitative of the present invention.

DETAILED DESCRIPTION OF EMBODIMENTS

Figure 1:
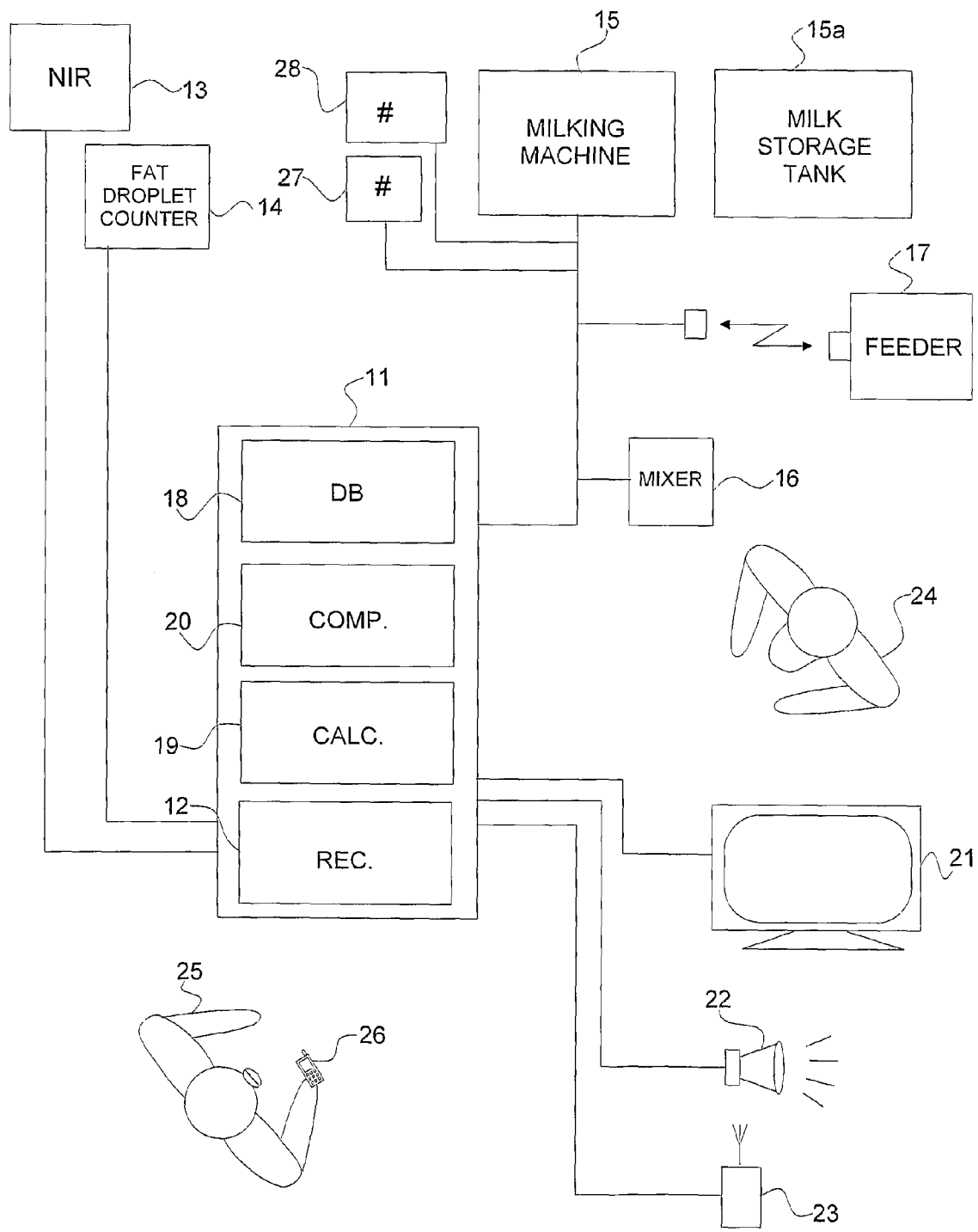
FIG. 1 displays schematically in a block diagram a dairy farm system comprising a management system according to an embodiment of the present invention.

A dairy farm system, which is shown in FIG. 1, comprises a milking machine 15 for milking animals, a milk storage tank 15a for collecting the milk produced, and a herd management system 11.

The milking machine 15 may be any kind of milking machine known in the art comprising teat cups and a source of vacuum, and it may be configured for manual attachment of the teat cups to the teats of an animal to be milked, or it may be equipped with a robot for automatic attachment of the teat cups to the teats of the animal. The dairy farm system may thus be any from an uncomplicated batch-wise milking system to a highly sophisticated robot milking system. Further, the dairy farm system may comprise more than one milking machine in order to milk more than one animal simultaneously, as well as milk transportation systems for bringing the milk into the milk storage tank 15.

The milk storage tank 15a is preferably equipped with cooling capacities in order to preserve the milk fresh. Further, the milk storage tank 15a may be provided with different compartments that will store different kind of milk, e.g. milk of different quality. Sophisticated milk transportation systems may be provided for automatically transport a milk of a given quality to a selected one of the different compartments.

The herd management system 11 is responsible for controlling the dairy farm system and optionally for processing and presenting various animal- or milk-related information, and comprises typically a microcomputer, suitable software, and a database 18 including information about each of the animals milked by the milking system, such as an identity of the animal, the milk production by the animal, and the quality of the milk produced by the animal. The database 18 may contain a lot of other animal-specific information such as e.g. when the respective animal was milked last time, when she was fed last time, her health, her expected milking time, etc.

The herd management system 11 is advantageously provided with output devices such as a display unit 21, or a loudspeaker 22 for outputting information to a farmer 24 located in vicinity of the herd management system 11 on the dairy farm. Further, it may be provided with a data communication network node or transmitter 23 for wired or wireless data or telecommunication with a PDA, other portable, or non-portable, device 26 of a farmer, technician or veterinarian 25 located at a remote place.

Further, the dairy farm system may comprise on-farm analyzer devices 13, 14, a feed mixer 16, a feeding device 17, animal-operating apparatus 27, and a milking equipment-operating apparatus 28, each connected to the herd management device 11.

The on-farm analyzer devices 13, 14 are capable of measuring, for each of the animals milked in the dairy farm system, values of protein and fat contents of milk from the animal. For instance, the device 13 may be a NIR instrument for measuring the protein content of the milk and the device 14 may be a fat droplet counting device.

Other measurement devices such as weighing devices and somatic cell counting devices may be provided for measuring various animal-related parameters. A device for performing the Milk Urea Nitrogen (MUN) test may advantageously be provided.

The feed mixer 16 is capable of mixing feed for each of the animals, and the feeding device 17 is capable of supplying feed to each of the animals. Both the feed mixer 16 and the feeding device 17 are capable of operating on an animal individual basis.

The animal-operating apparatus 27 is capable of performing an animal-related operation on an animal that is being or is to be milked by the milking machine 15. For instance, the animal-operating apparatus 27 may be a device suitable for administering a pharmaceutical drug, and/or giving a medicament or a diet additive, to an animal. Such device may be mounted at, or being an integral part of, a feeding device or station.

Alternatively, the animal-operating apparatus 27 is provided for disinfecting or cleaning the teats of an animal prior to being milked by the milking machine 15. Yet alternatively, the apparatus is a pre-milking device or other device for stimulating the milk ejection reflex and inducing milk let-down.

The milking equipment-operating apparatus 28 may be a device for diverting milk milked by the milking machine 15 to a selected one of different compartments of the milk storage tank. Alternatively, the apparatus may be a device for altering the operation of the milking system, e.g. altering a milking parameter such as the vacuum level. Yet alternatively, the apparatus may be a cleaning device for cleaning the teat cups of the milking system, the milking machine, or the entire dairy farm system, or a device for repairing one or several parts of the milking system.

Other animal-operating apparatuses and milking equipment-operating apparatuses may alternatively or additionally be provided.

The system of the present invention is provided to offer new approaches for improving the feed utilization and the milk production and the performance of the dairy farm system, while keeping the animals healthy and satisfied. The approaches are preferably at least partly carried out by means of software loadable into the herd management system 11 of the dairy farm system. It shall be appreciated by the person skilled in the art that some approaches may not need all the equipment and features as described with reference to FIG. 1. In such instance this equipment and features may be dispensed with.

According to the present invention, the herd management system 11 comprises a receiving module 12, a calculation module 19, and a comparison module 20 operative to perform various functions.

The receiving module 12 is provided for receiving, for each of the animals, a value of a protein content and a value of a fat, preferably butterfat, content of milk from the animal as milked on the dairy farm. The values of protein and fat contents may be measured by the on-farm analyzer devices 13, 14 and forwarded to the dairy herd system 11, or they might have been deduced in a laboratory, to which samples of milk have been sent. In the latter instance, the values of protein and fat contents may be entered manually by the farmer or they may be transmitted automatically to the herd management system 11.

The calculation module 19 is provided for calculating, for each of the animals, the ratio of the values of the protein and fat contents of milk from the animal, and the comparison module 20 is provided for fetching, for each of the animals, a reference protein/fat ratio from the database 18, and for comparing the calculated protein/fat ratio with the fetched reference protein/fat ratio. The database 18 stores to this end a reference protein/fat ratio for each of the animals.

Finally the herd management system 11 is adapted to control a selected one of the output devices 21-23 to notify, for each of the animals, the dairy farmer or other person related to the dairy farm depending on the outcome of the comparison of the calculated protein/fat ratio and the fetched reference protein/fat ratio. The notification may be made directly or at a later stage, e.g. as an entry in a database of the herd management system 11.

Preferably, a notification is made for an animal if the calculated protein/fat ratio differs from the reference protein/fat ratio by at least a first given amount. This indicates an altered rumen function for the animal, which can be an early warning that serious health problems may develop. Corrections may be performed in response to the notification.

If the calculated protein/fat ratio is higher than the reference protein/fat ratio by at least the first, given amount the notification may be accompanied with information that the feed supplied to the animal is short on fibers, and if the calculated protein/fat ratio is lower than the reference protein/fat ratio by at least the first given amount the notification may be accompanied with information that the feed supplied to the animal is short on energy.

The reference value is, for each of the animals, a normal value for a healthy and properly fed animal. The value may be determined, for each of the animals, based on historical protein/fat ratio data from milk from that animal, and optionally on historical protein/fat ratio data from milk from other ones of the animals, preferably from animals having similar breed, age and lactation phase as the animal, for which the reference protein/fat ratio is determined. In such manner, the inventive system may be fully automated.

The reference value may be determined from animals, which are housed on different dairy farms.

If the calculated protein/fat ratio differs from the reference protein/fat ratio by at least a second given amount for an animal, where the second amount is larger than the first amount, a veterinarian may be informed directly without delay, e.g. by notifying him remotely via the transmitter 23. The animal may have acidosis or laminitis.

Since the normal protein/fat ratio is very different for an animal during the lactation phase, the animals may be divided into different groups based on their lactation phases and optionally based on other parameters such as breed and age. Then the reference protein/fat ratio is determined to a single value for all animals in the same group.

Figure 2:
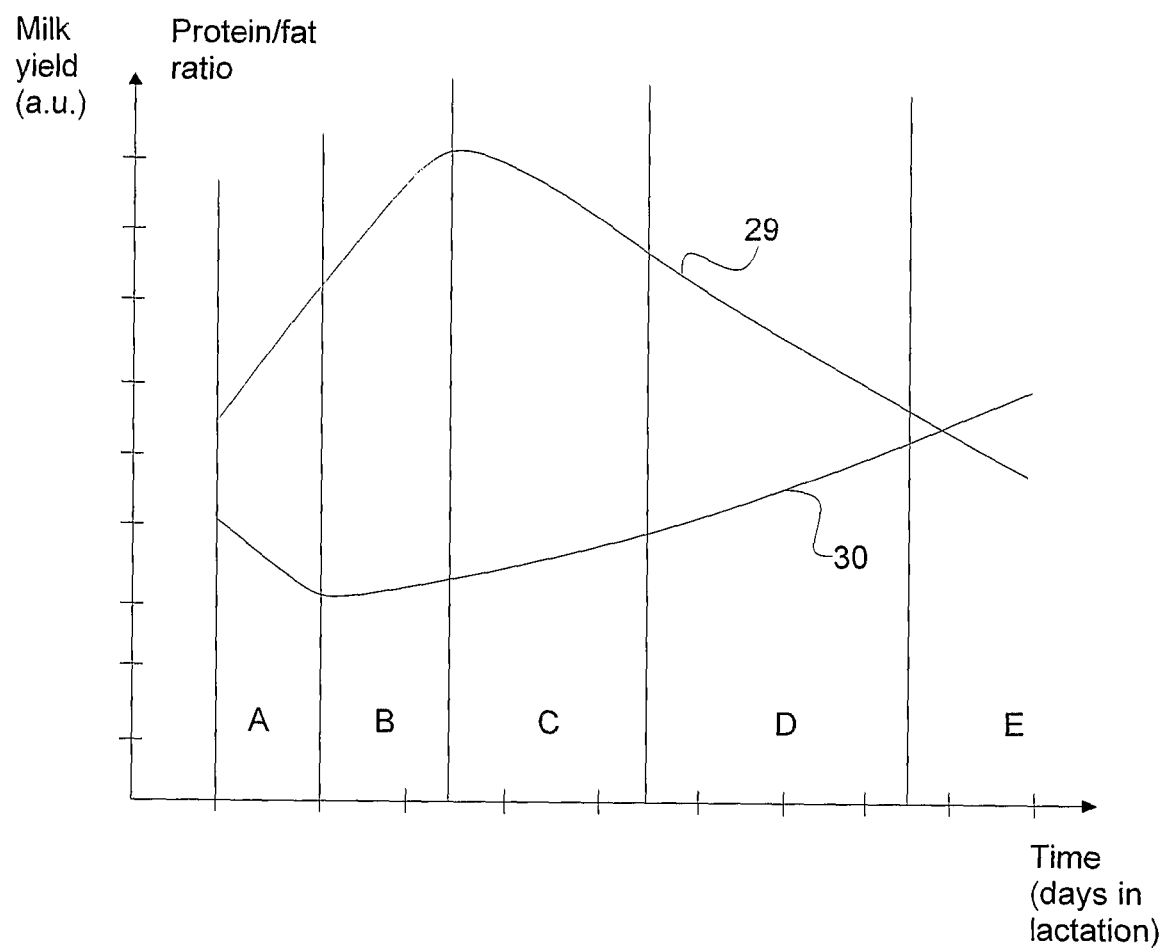
FIG. 2 is a schematic diagram of milk yield (a.u.) and protein-fat ratio (a.u.) as functions of time (days in lactation) for a milking animal.

FIG. 2 is a schematic diagram of milk yield (a.u.) and protein/fat ratio (a.u.) as functions of time (days in lactation) for a milking animal. The milk yield is denoted by 29 and the protein/fat ratio is denoted by 30. As can be seen the protein/fat ratio is almost the inverse of the milk yield. The protein/fat ratio decreases to about 50-60 days in lactation and increases thereafter. The milk yield peaks close to the point of time where the protein/fat ratio reaches its lowest value. Thus, the animals may be divided into the different groups A, B, C, D, E based on their number of days in lactation in accordance with the time frames as indicated in FIG. 2. All animals in the same group are then given the same reference value. Such approach facilitates the determination of reference protein/fat ratios, they have not to be updated so often, and larger numbers of animals with the same reference protein/fat ratio give better statistics when determining a proper reference protein/fat ratio.

Further, the absolute values of the protein and fat contents may give additional information of the status of an animal. Thus, the comparison module 20 is provided for fetching, for each of the animals, a reference value for the protein content 18 and/or a reference value for the fat content from the database, and for comparing, for each of the animals, the received value of the protein content with the fetched reference value for the protein content and/or for comparing the received value of the fat content with the fetched reference value for the fat content. Finally, a selected one of the output devices 21-23 is controlled to notify, for each of the animals, the dairy farmer 24 depending on the outcome of the comparison of the received value of the protein content and the fetched reference value for the protein content and/or the received value of the fat content and the fetched reference value for the fat content.

Still further, the feed mixer 16, the feeding device 17, animal-operating apparatus 27, and/or the milking equipment-operating apparatus 28 may be controlled, for each of the animals, to perform various actions depending on the comparison of the calculated protein/fat ratio and the fetched reference protein/fat ratio.

The feed mixer 16 may be controlled to automatically mix, for each of the animals, feed for that animal depending on the outcome of the comparison of the calculated protein/fat ratio and the fetched reference protein/fat ratio. The feed mixer is particularly controlled to increase, for each of the animals, a fiber content in the feed for that animal if the calculated protein/fat ratio is higher than the reference protein/fat ratio by at least a given amount, and to increase, for each of the animals, an energy content in the feed for that animal if the calculated protein/fat ratio is lower than the reference protein/fat ratio by at least the given amount.

The calculated protein/fat ratio may serve a good indicator of the efficiency of the feed mixer 16 and on the homogeneity of the feed mix.

The feeding device 17 may be controlled to supply, to each of the animals, the respective feed as mixed by the feed mixer 16. Alternatively, the feeding device 17 is controlled to supply, for each of the animals, feed to that animal depending on the outcome of the comparison of the calculated protein/fat ratio and the fetched reference protein/fat ratio.

The animal-operating apparatus 27 may be controlled to perform, for each of the animals, an animal-related operation on that animal depending on the outcome of the comparison of the calculated protein/fat ratio and the fetched reference protein/fat ratio. The animal-related operation may comprise to administer a pharmaceutical drug, and/or give a medicament or a diet additive, to the animal.

The milking equipment-operating apparatus 28, finally, may be controlled to perform, for each of the animals, a milking equipment-related operation in connection with the milking of that animal depending on the outcome of the comparison of the calculated protein/fat ratio and the fetched reference protein/fat ratio.

It shall be appreciated that the various features of the present invention may be combined to reach still further versions and variants of the invention.

The invention thus being described facilitates herd management, improves herd nutrition and health, optimizes feed utilization, and increases productivity in dairy farming.

The invention claimed is:

1. A system for managing animals on a dairy farm, comprising:
an on-farm analyzer system (13,14) provided for measuring, for each of said animals, values of protein and fat contents of milk from each said animal;
receiving means (12) provided for receiving from the on-farm analyzer, for each of said animals, the value of the protein content and the value of the fat content of milk from the animal as milked on said dairy farm;
calculating means (19) provided for calculating, for each of said animals, a protein/fat ratio from a ratio of the received values of said protein and said fat contents of milk from the animal;
comparing means (20) provided for fetching, for each of said animals, from a database (18) a reference protein/fat ratio, and for comparing the calculated protein/fat ratio with the fetched reference protein/fat ratio; and
notifying means (21-23), notifying, for each of said animals, a dairy farmer (24) of said dairy farm when an outcome of the comparison of the calculated protein/fat ratio and the fetched reference protein/fat ratio indicates a need to adapt feed to be supplied to said animal,
wherein said system is fully automated.

2. The system of claim 1, wherein
said notifying means is provided for notifying, for each of said animals, the dairy farmer if the calculated protein/fat ratio differs from the reference protein/fat ratio by at least a first given amount, and
the notifying means is one of a display unit (21), a loudspeaker (22), and a transmitter (23).

3. The system of claim 2, wherein said notifying means is provided for informing, for each of said animals, the dairy farmer that the feed supplied to the animal is unbalanced if the calculated protein/fat ratio is higher than the reference protein/fat ratio by at least a given amount.

4. The system of claim 2, wherein said notifying means is provided for informing, for each of said animals, the dairy farmer that the feed supplied to the animal is unbalanced if the calculated protein/fat ratio is lower than the reference protein/fat ratio by at least a given amount.

5. The system of claim 2, wherein said notifying means (23) is provided for notifying, for each of said animals, a veterinarian (25) if the calculated protein/fat ratio differs from the reference protein/fat ratio by at least a second given amount, said second amount being larger than said first amount.

6. The system of claim 1, wherein, for each of said animals, said reference protein/fat ratio is a normal value for a healthy and properly fed animal.

7. The system of claim 1, wherein,
said calculating means is provided for calculating, for each of said animals, said reference protein/fat ratio based on:
historical protein/fat ratio data from milk from the animal, and
on historical protein/fat ratio data from milk from other ones of said animals, from animals having similar breed, age and lactation phase as the animal and which animals are housed on said dairy farm.

8. The system of claim 1, wherein said animals belong to different groups based on their lactation phases and said reference protein/fat ratio is the same for all animals in the same group.

9. The system of claim 1, wherein said on-farm analyzer system comprises a NIR instrument (13).

10. The system of claim 1, wherein said on-farm analyzer system comprises a fat droplet counting device (14).

11. The system of claim 1, wherein said fat is butterfat.

12. The system of claim 1, wherein,
said comparing means is provided for fetching, for each of said animals, from the database a reference value for the protein content and/or a reference value for the fat content, and for comparing, for each of said animals, the received value of the protein content with the fetched reference value for the protein content and for comparing the received value of the fat content with the fetched reference value for the fat content; and
said notifying means is provided for notifying, for each of said animals, the dairy farmer of said dairy farm depending on an outcome of the comparison of the received value of the protein content and the fetched reference value for the protein content and the received value of the fat content and the fetched reference value for the fat content.

13. The system of claim 1, futher comprising a feed mixer (16) provided for mixing, for each of said animals, feed for said animal depending on the outcome of the comparison of the calculated protein/fat ratio and the fetched reference protein/fat ratio.

14. The system of claim 13, wherein said feed mixer is provided for changing, for each of said animals, a fiber content in the feed for said animal if the calculated protein/fat ratio is higher than the reference protein/fat ratio by at least a given amount.

15. The system of claim 13, wherein said feed mixer is provided for changing, for each of said animals, a protein type content and/or an energy content in the feed for said animal if the calculated protein/fat ratio is lower than the reference protein/fat ratio by at least a given amount.

16. The system of claim 13, further comprising a feeding device (17) provided for supplying, to each of said animals, the respective feed as mixed by said feed mixer.

17. The system of claim 1, further comprising a feeding device capable of supplying different kind of feed to said animals, wherein said feeding device is provided for supplying, for each of said animals, feed to said animal depending on the outcome of the comparison of the calculated protein/fat ratio and the fetched reference protein/fat ratio.

18. The system of claim 1, further comprising animal-operating apparatus (27) provided for performing, for each of said animals, an animal-related operation on that animal depending on the outcome of the comparison of the calculated protein/fat ratio and the fetched reference protein/fat ratio.

19. The system of claim 18, wherein said animal-operating apparatus (27) is a device suitable for administering a pharmaceutical drug, a medicament, and a diet additive, to the animals.

20. The system of claim 1, further comprising a milking equipment-operating apparatus (28) provided for performing, for each of said animals, a milking equipment-related operation in connection with the milking of said animal depending on the outcome of the comparison of the calculated protein/fat ratio and the fetched reference protein/fat ratio.

21. A method for managing animals on a dairy farm, comprising the steps of:
  measuring, with an on-farm analyzer system (13,14), for each of said animals, values of protein and fat contents of milk from each said animal;
  receiving from the on-farm analyzer system, for each of said animals, the value of the protein content and the value of the fat content of milk from the animal as milked on said dairy farm;
  calculating, for each of said animals, a protein/fat ratio from a ratio of the values of said protein and fat contents of milk from the animal;
  fetching, for each of said animals, a reference protein/fat ratio from a database (18);
  comparing, for each of said animals, the calculated protein/fat ratio with the fetched reference protein/fat ratio; and
  notifying, through a notifying means, for each of said animals, a dairy farmer (24) of said dairy farm when an outcome of the comparison of the calculated protein/fat ratio and the fetched reference protein/fat ratio indicates a need to adapt feed to be supplied to the each said animal,
  wherein each of said receiving, calculating, fetching, comparing, and notifying steps is fully automated.

22. The method of claim 21, wherein,
  the dairy farmer is notified, for each of said animals, if the calculated protein/fat ratio differs from the reference protein/fat ratio by at least a given amount, the notifying means being one of a display unit (21), a loudspeaker (22), and a transmitter (23).

23. The method of claim 21, wherein, for each of said animals, feed for said animal is mixed depending on the outcome of the comparison of the calculated protein/fat ratio and the fetched reference protein/fat ratio.

24. The method of claim 21, wherein, for each of said animals, feed is supplied to said animal depending on the outcome of the comparison of the calculated protein/fat ratio and the fetched reference protein/fat ratio.

25. A system for managing animals on a dairy farm, comprising:
  an on-farm analyzer system (13, 14) provided for measuring, for each of said animals, values of protein and fat contents of milk from each said animal;
  receiving means (12) provided for receiving from the on-farm analyzer the value of the protein content and the value of the fat content of milk from each said animal as milked on said dairy farm;
  calculating means (19) provided for calculating a protein/fat ratio, for each said animal, from a ratio of the received values of said protein and said fat contents of milk from each said animal;
  comparing means (20) provided for fetching from a database (18) a reference protein/fat ratio, and, for each said animal, comparing the calculated protein/fat ratio with the fetched reference protein/fat ratio for said animal; and
  notifying means (21-23) notifying, for each of said animals, a dairy farmer (24) of said dairy farm when an outcome of the comparison of the calculated protein/fat ratio and the fetched reference protein/fat ratio indicates an altered rumen function for said animal and a need to adapt feed to be supplied to said animal,
  wherein said system is fully automated.

26. The system of claim 25, wherein,
  said outcome of the comparison of the calculated protein/fat ratio and the fetched reference protein/fat ratio for said animal indicates the need to adapt the feed to be supplied to said animal for each of:
  altering fiber content of the feed,
  altering energy content of the feed,
  supplementing the feed with a pharmaceutical drug,
  supplementing the feed with a medicament, and
  supplementing the feed with a diet additive.

\* \* \* \* \*